United States Patent [19]

Seiden et al.

[11] Patent Number: 4,996,074
[45] Date of Patent: Feb. 26, 1991

[54] TAILORED BETA-PRIME STABLE TRIGLYCERIDE HARDSTOCK

[75] Inventors: Paul Seiden; Robert L. White, both of Cincinnati, Ohio

[73] Assignee: The Procter & Gamble Company, Cincinnati, Ohio

[21] Appl. No.: 270,314

[22] Filed: Nov. 14, 1988

[51] Int. Cl.$^5$ ............................................. A23D 9/00
[52] U.S. Cl. .................................... 426/601; 426/606; 426/607; 426/611; 426/804
[58] Field of Search ............... 426/607, 804, 601, 606, 426/611

[56] References Cited

U.S. PATENT DOCUMENTS

| | | | |
|---|---|---|---|
| 3,012,890 | 12/1961 | Dutton et al. | 426/607 X |
| 3,597,230 | 8/1971 | Colby et al. | 426/607 |
| 3,600,186 | 8/1971 | Mattson et al. | |
| 3,809,711 | 5/1974 | Yetter et al. | |
| 3,809,712 | 5/1974 | Yetter et al. | |
| 4,005,195 | 1/1977 | Jandacek et al. | |
| 4,005,196 | 1/1977 | Jandacek et al. | |
| 4,055,679 | 10/1977 | Kattenberg et al. | |
| 4,247,471 | 1/1981 | Klein et al. | 260/410.7 |
| 4,447,462 | 5/1984 | Tafuri et al. | |
| 4,588,604 | 5/1986 | Baker et al. | |
| 4,702,298 | 10/1987 | Wieske et al. | |

FOREIGN PATENT DOCUMENTS

| | | |
|---|---|---|
| 200803 | 11/1986 | European Pat. Off. |
| 0233856 | 9/1987 | European Pat. Off. |
| 0236288 | 9/1987 | European Pat. Off. |
| 2570388 | 3/1986 | France |
| 0269904 | 8/1988 | Japan |
| 1603002 | 1/1981 | United Kingdom |

OTHER PUBLICATIONS

R. J. Jandacek and M. R. Webb, "Physical Properties of Pure Sucrose Octaesters", *Chemistry and Physics of Lipids*, vol. 22, No. 2, pp. 163–176, (9/78).
E. S. Lutton, "Lipid Structures", *Journal of the American Oil Chemists' Society*, vol. 49, No. 1, pp. 1–9 (1972).
E. S. Lutton, "Binary Systems from Palmitic-Stearic Triglycerides", *Journal of the American Oil Chemists' Society*, vol. 44, No. 5, pp. 303–304, (11/8/66).
E. S. Lutton and F. R. Hugenberg, "Beta Phase of 2-Stearoyldipalmitin", *Journal of Chemical & Engineering Data*, vol. 5, No. 4, pp. 489–490, (10/60).
E. S. Lutton and F. S. Jackson, "The Polymorphism of Synthetic and Natural 2-Oleyldipalmitin", 72 *Journal of American Chemical Socity*, pp. 3254–3257 (1950).
N. V. Lovegren, et al., "Properties of 2-Oleodipalmitin, 2-Elaidodipalmitin, and Some of Their Mixtures", *Journal of American Oil Chemists' Society*, vol. 48, pp. 116–120 (9/14/70).
E. S. Lutton and A. J. Fehl, "Polymorphism of 1-Behenoyldistearin and 2-Stearoyldibehenin", *Journal of the American Oil Chemists' Society*, vol. 49, No. 5, pp. 336–337 (1972).
B. K. Tan and R. J. Hamilton, "Glyceride Analysis of Palm Oil After Solvent Fractionation", *Journal of American Oil Chemists' Society*, pp. 1–5 (1/81).
V. Gibon et al., "Polymorphism and Intersolubility of Some Palmitic, Stearic, and Oleic Triglycerides: PPP, PSP and POP".
Perotti, "Sucrose Esters and Food Products", *Inustrie Alimentari* 14(1), pp. 77–81 (abstract only) (1975).

Primary Examiner—Donald E. Czaja
Assistant Examiner—Evan Federman
Attorney, Agent, or Firm—Ronald L. Hemingway; Julius P. Filcik; Richard C. Witte

[57] ABSTRACT

A stable beta-prime tailored triglyceride hardstock is disclosed which exhibits superior beta-prime stability and yields improved texture, stability, oil retention, and/or flavor display when incorporated into various food products.

The beta-prime stable hardstock of the present invention comprises: (a) from about 45% to about 98% of 2-Stearoyldipalmitin (PSP) triglycerides: (b) from about 2% to about 55%, of 1-Palmitolydistearin (PSS) triglycerides; (c) less than about 7% of tripalmitin (PPP) triglycerides; (d) less than about 7% of tristearin (SSS) triglycerides; (e) less than about 3% of diglycerides; (f) less than about 10% of total PPP plus SSS triglycerides; and (g) less than about 10% of the fatty acids of the total triglycerides and diglycerides being unsaturated.

29 Claims, 1 Drawing Sheet

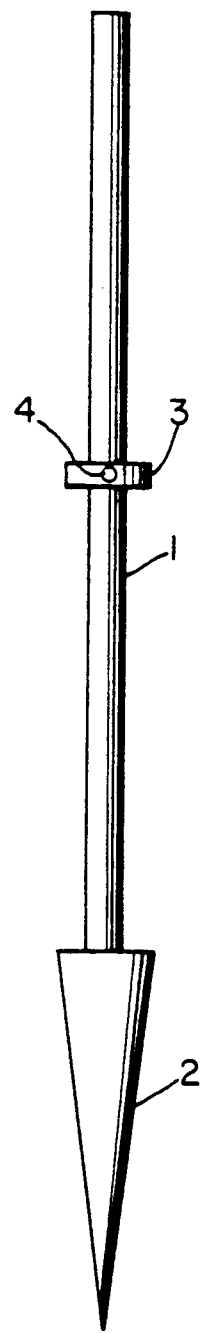

TAILORED BETA-PRIME STABLE TRIGLYCERIDE HARDSTOCK

TECHNICAL FIELD

The present invention relates to a tailored beta-prime stable triglyceride hardstock and to various food products suitable for its use therein.

BACKGROUND INFORMATION

Conventional plastic shortenings are essentially composed of high- and intermediate-melting solid fats or mixtures thereof, e.g., "hardstocks", and liquid oils which have been processed by various techniques which make the product plastic and workable at room temperature. Hardstocks and hardstock stabilizers are incorporated into various other food products, in addition to conventional plastic shortenings, including, but not limited to, fluid shortenings, frostings, icings, and peanut butter. Thus, it is well known in the art that certain kinds of fat crystals, most notably the beta-prime crystals, have the capacity to form a rigidly interlocking structure when suspended in a liquid component if the solids are present in sufficient amounts.

It is, therefore, important that the hardstocks or stabilizers added to food products be of the proper crystal type. For example, a shortening that contains solids that transform or recrystallize into the beta crystal phase often tends to produce graininess. To provide the most acceptable commercial plastic shortenings which have good creaming ability and retain their appearance, volume, and performance characteristics under expected storage conditions, it is necessary that the solid glycerides crystallize and remain in the beta-prime crystal form In general, the method of attaining the beta-prime crystal form desired for various food products is to add a suitable beta-prime-tending hardstock or hardstock stabilizer. These conventional beta-prime tending type hardstocks or stabilizers are produced from palm oil, cottonseed oil, rapeseed oil, corn oil, peanut oil, and certain fish oils. These hardstocks, however, contain 20%–30% glycerides which are not beta-prime stable, for example, tristearin, tripalmitin, and 1,3-diglycerides, which are deleterious to product performance These glycerides, and most others, are not stable in the beta-prime crystal phase. Conventional hardstocks, which contain such glycerides, will undergo polymorphic transformations and crystal size changes upon storage and/or upon temperature variations. This results in poor appearance, volume and performance in food compositions which contain such hardstocks.

The present invention consists of a new uniquely stable beta-prime hardstock which exhibits superior beta-prime stability and yields improved texture, stability, oil retention, and/or flavor display when incorporated into various food products. This is achieved by creating the significantly more beta-prime stable hardstock of the present invention by tailoring the triglyceride molecules to position-specific compositions by the processes such as those described herein.

It is therefore an object of this invention to create an improved beta-prime stable hardstock exhibiting superior product appearance, texture, taste, and/or flavor display.

It is another object of this invention to provide a beta-prime stable hardstock which exhibits excellent compatibility with other beta-prime-crystal-tending hardstocks such as fully hydrogenated high-erucic acid rapeseed oil and high-behenic acid rapeseed oil, along with good compatibility with reduced- or non-caloric fats which are either non-digestible or are only partially-digestible.

It is an additional object of the present invention to provide a beta-prime stable hardstock which, when incorporated into shortening or peanut butter, more effectively entraps liquid oil components, thereby providing improved storage stability of the peanut butter and the shortening even at elevated temperatures (90° F.–100° F.; 32° C.–38° C.) or even when the hardstock is incorporated into the food products in reduced concentrations.

It is a further object of this invention to provide a beta-prime stable hardstock which, when incorporated into conventional plastic shortenings, yields a plastic shortening which exhibits a significant reduction in crystal size having improved creaminess and texture.

It is likewise an object of this invention to provide a beta-prime stable hardstock which, when incorporated into shortenings, allows the use of less intermediate melting constituents (which are generally high in saturated fatty acids) and thereby yields a high quality shortening with a reduction in saturated fatty acid content.

It is also an object of the present invention to provide a hardstock which, when incorporated into peanut butter, will yield a peanut butter exhibiting reduced stickiness in the mouth of consumers upon ingestion and will enable the production of a soft textured peanut butter exhibiting improved storage stability and reduced oil separation.

It is another object of the present invention to provide a hardstock which may be used as a base or stabilizer in various cosmetic and pharmaceutical formulations.

These and other objects of the invention will be made clear by the disclosure herein.

All percentages and ratios are by weight unless otherwise indicated.

BRIEF DESCRIPTION OF THE DRAWING

The Drawing illustrates the penetrating device used to measure the penetration (firmness) of the reduced-calorie shortenings described herein as suitable for utilizing the hardstock of the present invention.

SUMMARY OF THE INVENTION

In accordance with the present invention, a significantly more stable beta-prime tailored triglyceride hardstock (as compared to conventional hardstocks) is disclosed which exhibits superior beta-prime stability and yields improved texture, stability, oil retention, and/or flavor display when incorporated into various food products such as shortening, frosting, icing, and peanut butter.

From about 0.1% to about 20% of the beta-prime stable hardstock of the present invention may be successfully incorporated into various food, cosmetic, or pharmaceutical products which contain lipid materials. The term "lipid", as used herein, particularly describes triglyceride fats and oils as well as non- or partially-digestible fatty materials as defined hereinbelow. "Lipid", as used herein, encompasses fats and fat-like materials and includes those substances which are relatively insoluble in water but are miscible with fat solvents (including, but not limited to, benzene, chloroform, acetone, and ether), and which are related either actually or potentially to fatty acid esters.

The beta-prime triglyceride hardstock is preferably produced by the crystal fractionation, most preferably by the solvent or detergent fractionation, of certain naturally occurring source oils. The source oils must contain high concentrations of PUP and PUU triglycerides. Said source oils are subjected to fractionation in order to separate therefrom undesirable trisaturated triglycerides (for example, tripalmitin, hereinafter PPP, and tristearin, hereinafter SSS), triunsaturated triglycerides, and diglycerides and leave behind the desirable PUP and PUU intermediates. Said PUP and PUU triglyceride intermediates are finally hydrogenated to yield 2-Stearoyldipalmitin (hereinafter PSP) and 1-Palmitoyldistearin (hereinafter PSS) triglycerides, which are the main constituents of the beta-prime stable tailored triglyceride hardstock of the present invention.

"P", as used herein, is palmitic acid.

"U", as used herein, is an unsaturated fatty acid having 18 carbon atoms.

"S", as used herein, is stearic acid.

The beta-prime stable hardstock of the present invention therefore comprises: (a) from about 45% to about 98%, preferably from about 60% to about 92%, most preferably from about 60% to about 85%, of PSP triglycerides; (b) from about 2% to about 55%, preferably from about 8% to about 40%, most preferably from about 15% to about 40%, of PSS triglycerides; (c) less than about 7%, and preferably less than about 4%, of PPP triglycerides; (d) less than about 7%, and preferably less than about 4%, of SSS triglycerides; (e) less than about 3%, preferably less than 1%, and most preferably less than about 0.2%, of diglycerides; (f) less than about 10%, and preferably less than about 6%, of total PPP plus SSS triglycerides; and (g) less than about 10%, preferably less than about 2%, of the fatty acids of the total triglycerides and ciglycerides being unsaturated.

DETAILED DESCRIPTION OF THE DRAWING

The Drawing illustrates the penetrating device used to measure the penetration (firmness) of the reduced calorie shortenings described herein as suitable for utilizing the hardstock of the present invention.

The penetrating device comprises a shaft 1 and needle 2 (or "cone"). A 9" long hollow steel rod having a 3/16" outer diameter is used for the shaft. At the end of the shaft is a 2" long hollow stainless steel needle or cone. The pointed end of the needle has a 1/32" diameter and the enlarged end has a 19/32" diameter. The needle can be unscrewed from the shaft to insert weights into the hollow needle. A magnesium collar 3 with a set screw 4 is positioned around the shaft, about 4¼" from the end opposite the needle. The collar is 7/16" in diameter and ⅛" thick. The penetrating device as a whole, including the collar, must weigh 47 grams.

DETAILED DESCRIPTION OF THE INVENTION

The stable beta-prime triglyceride hardstock of the present invention is preferably produced by subjecting certain source oils which contain high concentrations of PUP and PUU triglycerides to crystal fractionation, preferably solvent fractionation. Such fractionation processes as described hereinbelow separate undesirable trisaturated triglycerides (e.g., PPP, SSS), triunsaturated triglycerides (which become trisaturated triglycerides upon hydrogenation), and diglycerides from the source oil and leave behind the desirable PUP and PUU triglycerides, which are intermediate triglycerides in the process of forming the desirable PSP and PSS triglycerides. The PUP and PUU intermediate triglycerides which remain after the fractionation of the source oils are simply hydrogenated to yield the desirable PSP and PSS triglycerides which are the main constituents in the beta-prime stable hardstock of the present invention The PUP and PUU triglyceride intermediates are most preferably isolated from the source oils by the crystal fractionation process described below. There are, however, various methods to synthesize, isolate, or otherwise obtain the PUP and PUU triglyceride intermediates which are acceptable in the practice of the present invention. The chemical synthesis, pathway, or process used to derive the PUP and PUU triglyceride intermediates is not of any consequence; it is only important that sufficient PUP and PUU triglycerides are generated and available for hydrogenation in order to yield a composition containing sufficient amounts of PSP and PSS triglycerides upon hydrogenation.

The beta-prime crystalline morphology and stability of PSP triglycerides has been identified and discussed by E. S. Lutton and F. R. Hugenberg in "Beta Phase of 2-Stearoyldipalmitin," *Journal of Chemical and Engineering Data*, Vol. 5, No. 4, pp. 489–90 (1960), and also by E. S. Lutton in "Lipid Structures," *Journal of the American Oil Chemists' Society*, Vol. 49, No. 1, pp. 1–9 (1972), both incorporated by reference herein. The relative beta-prime crystalline morphology and stability of both PSP and PSS triglycerides is likewise discussed by E. S. Lutton in "Binary Systems from Palmitic-Stearic Triglycerides", *Journal of the American Oil Chemists' Society*, Vol. 44, No. 5, pp. 303–304 (1966), also incorporated herein by reference.

In order to produce the beta-prime stable tailored triglyceride hardstock, a suitable source oil must undergo the fractionation processes described herein. Suitable source oils must contain high concentrations of PUP and PUU triglycerides, most preferably at least from about 45% to about 98% of PUP triglycerides and at least from about 2% to about 55% PUU triglycerides. Certain naturally occurring vegetable oils exhibit this composition and include, but are not limited to, palm oil, cottonseed oil, stillingia tallow, piquia fat, and mixtures thereof. Certain genetically engineered vegetable oils could be fashioned to exhibit the required concentration of PUP and PUU triglycerides. One of these is a genetically engineered soybean oil, $A_6$, described by E. G. Hammond and W. R. Fehr in *Biotechnology for the Oils and Fats Industry*, Edited by C. Ratledge et al., Published by American Oil Chemist Society, Copyright 1984, pp. 89–96, incorporated by reference herein.

The high concentrations of PUP and PUU found in the source oils must be separated from the undesirable constituents therein, namely trisaturated triglycerides (PPP, SSS), triunsaturated triglycerides, and diglycerides. A preferred method of separation is crystalline fractionation, most preferably solvent crystalline fractionation. Preferred methods of solvent fractionation are explained in Examples I, II, and IV herein. A method of non-solvent fractionation is set forth in Example III herein. Other methods of solvent and non-solvent fractionation of naturally occurring source oils are illustrated in the following references, all incorporated by reference herein: U.S. Pat. No. 4,588,604 to Baker and Weitzel, (assigned to The Procter & Gamble Company), issued May 13, 1986 (solvent fractionation of palm oil); E. S. Lutton, and F. L. Jackson, "The Polymorphism of Synthetic and Natural 2-Oleyldipalmitin," *Journal of the American Chemical Society*, Vol. 72, pp. 3254–57, (1950) (solvent fractionation of stillingia tallow and piquia fat); U.S. Pat. No. 4,447,462 to Tafuri and Tao (assigned to The Procter & Gamble Company), issued May 8, 1984 (solventless, two-step thermal fractionation of palm oil); and U.S. Pat. No. 4,247,471 to Klein and Lacome (assigned to Lesieur-Cotelle & Associes, S.A., Hauts de Sene, France), issued Jan. 27, 1981 (solvent fractionation of palm oil).

In addition to the fractionation methods set forth immediately above, several methods of separation are available to remove the undesirable diglycerides from the source oils. One suitable method is a European Patent Publication No. 0,269,904 to Matsumoto et al. (assigned to Asahi Denka Kogyo Kabushiki Kaisha), published June 8, 1988, incorporated by reference herein. Deodorization or vacuum distillation, preferably high vacuum distillation, are also suitable methods of separating undesirable diglycerides from the source oils.

While many methods of fractionation are known in the art and can be successfully used to generate the PUP and PUU intermediate triglycerides of the present invention, solvent fractionation is preferred over non-solvent fractionation because it can more satisfactorily neutralize trisaturated and triunsaturated triglyceride constituents. Various solvents are known in the art for use in fractionation of triglycerides. Two important examples for achieving the separation required for the present invention are hexane and acetone. Hexane may be more preferred from a cost-savings standpoint, due to the relative inexpensiveness and high availability of hexane. Nevertheless, the use of acetone as a solvent is preferred from the standpoint of effectiveness, since acetone produces better separation, thereby yielding an increased amount of the PUP and PUU triglyceride intermediates which are purer and exhibit larger crystals. In addition, detergent fractionation, a type of non-solvent fractionation, has shown excellent results in isolating the PUP and PUU intermediates from the source oils because that process tends to more completely separate the liquid portion of fractionating solutions from the PUP and PUU triglyceride crystals. Other types of non-solvent fractionation, for example multiple non-solvent fractionation and pressure fractionation, are also acceptable.

It is important to understand that numerous methods of fractionation are suitable for use herein and that various orders of successive particular fractionation steps to remove different types of the undesirable components are suitable. Certain preferred methods and order of particular fractionation steps depend upon the source oil that is being used and its particular fatty acid and glyceride composition. As a general rule, any method of fractionation, as well as any order of particular fractionation steps, can be satisfactorily used on any suitable oil, so long as it removes the requisite amount of undesirable trisaturated triglycerides (PPP, SSS), trisaturated triglycerides, and diglycerides, and yields a sufficient amount of PUP and PUU triglyceride intermediates which can then go on to be hydrogenated to yield PSP and PSS triglycerides.

A solventless fractionation process is disclosed herein in Example III. This process is preferably used in conjunction with the fractionation steps of source oils, either before or after the other solvent or non-solvent fractionation steps. This process is preferably used sometime during the process of isolating the PUU and PUP intermediates because it is particularly effective in removing undesirable tripalmitin triglycerides.

Various methods are available and acceptable for obtaining the desirable PUP and PUU triglyceride intermediates, although the isolation of these intermediates from naturally occurring source oils by fractionation is preferred. For example, several methods are disclosed for chemically synthesizing the desirable intermediates and include those disclosed in U.S. Pat. Nos. 3,809,711 and 3,809,712, both to Yetter (both assigned to The Procter & Gamble Company), both issued May 7, 1974; and 3,012,890 to Dutton and Scholfield (assigned to U.S. Secretary of Agriculture), issued Dec. 12, 1961, all incorporated by reference herein. Other suitable methods of synthesis are described by E. S. Lutton and F. L. Jackson in their article "The Polymorphism of Synthetic and Natural 2-Oleyldipalmitin," *Journal of the American Chemical Society*, Vol. 72, pp. 3254–57 (1950), and by N. V. Lovegren et al. in "Properties of 2-Oleodipalmitin, 2-Elaidodipalmitin and Some of Their Mixtures," *Journal of American Oil Chemists' Society*, Vol. 48, pp. 116–120 (1970), both incorporated by reference herein.

Other methods of obtaining the desirable PUP and PUU triglyceride intermediates are available and suitable for use in making the beta-prime stable hardstock of the present invention. For example, position-specific enzymatic esterification can be utilized to obtain PUP and PUU triglycerides and genetic engineering could also be employed to produce vegetable source oils containing a high concentration of PUP and PUU triglycerides. Various sources of commercially fractionated vegetable oils are available which contain the requisite concentrations of palmitic acid and PUP and PUU triglycerides; the commercially fractionated palm oil hydrogenated in Example V is one such example thereof.

As has been previously stated, any method of isolating, by fractionation or otherwise, chemically synthesizing, or otherwise obtaining the desirable PUP or PUU triglyceride intermediates is suitable for processing the beta-prime stable tailored triglycerid hardstock of the present invention, so long as the method utilized sufficiently results in a hardstock with the particular requisite composition as disclosed herein. In other words, it is only necessary that, after the PUP and PUU triglyceride intermediates, regardless of their source, have been hydrogenated to yield PSP and PSS triglycerides, the resulting tailored triglyceride hardstock comprises from about 45% to about 98%, preferably from about 60% to about 92%, most preferably from about 60% to about 85%, PSP triglycerides; from about 2% to about 55%, preferably from about 8% to about 40%, most preferably from about 15% to about 40%, PSS triglycerides; less than about 7%, preferably less than about 4%, PPP triglycerides; less than about 7%, preferably less than about 4%, SSS triglycerides; less than about 3%, preferably less than about 1%, and most preferably less than about 0.2%, diglycerides; less than about 10%, preferably less than about 6% total PPP and SSS triglycerides; and less than about 10%, preferably less than about 2%, of the fatty acids of the total triglycerides and diglycerides being unsaturated.

The hydrogenation of the PUP and PUU triglyceride intermediates to yield the desirable PSP and PSS triglyceride products may be by any of a number of suitable methods known in the art. Particularly preferred is that disclosed in Example V herein and also suitable are those disclosed in U.S. Pat. Nos. 4,087,564 to Poot et al. (assigned to Lever Brothers Company), issued May 2, 1978; 4,702,928 to Wieske et al. (assigned to Internationale Octrooi Maatschappi, "Octropa" B. V., Rotterdam, Netherlands), issued Oct. 27, 1987; and 4,055,679 to Kattenberg et al. (assigned to Lever Brothers Company), issued Oct. 25, 1977; all incorporated by reference herein.

From about 0.1% to about 20% of the hardstock resulting after the hydrogenation of the PUP and PUU intermediate triglycerides may be successfully incorporated into various food, cosmetic or pharmaceutical products which contain lipid material, particularly conventional triglyceride fats or oils and/or non- or partially-digestible fatty materials. Especially suitable for use as the non- or partially-digestible fatty materials are the sugar or sugar alcohol fatty polyol polyesters defined hereinbelow. Said hardstock is beta-prime stable and crystallizes very rapidly, thereby exhibiting unique functionality and yielding, when incorporated in various food products, improved texture, stability, oil retention, and/or flavor display. Food products especially suitable for inclusion of the beta-prime stable hardstock of the present invention are fatty food products, including, but not limited to, plastic and fluid shortening, peanut butter, frosting, and icing. When incorporated into shortenings and peanut butter, the hardstock of the present invention more effectively entraps the liquid oil components, thereby improving their storage stability at elevated temperatures (90° F.–100° F.; 32° C.–38° C.) or even when the hardstock is incorporated into the food products in reduced concentrations.

In shortenings, the concentration of the hardstock of the present invention should be from about 3% to about 12%, preferably from about 4% to about 9%, but said hardstock should replace at least 20% of the triglyceride trisaturates (e.g., PPP and SSS). All types of shortenings containing this beta-prime stable hardstock are of an improved quality and yield a significant reduction in saturated fatty acid content. Plastic shortenings containing the hardstock of the present invention exhibit a reduction in crystal size and improved creaminess and texture. In peanut butter, the concentration of the hardstock of the present invention should be from about 0.3% to about 2%, preferably from about 0.5% to about 1.4%.

Highly hydrogenated high erucic acid rapeseed oil which is shown in Example VI is an additional example of a beta-prime tending hardstock suitable for use in various food products in combination with the hardstock of the present invention. When the stable beta-prime PSP/PSS hardstock of the present invention is used in combination with highly hydrogenated (Iodine Value less than 20, preferably less than 10) high erucic acid (preferably at least about 40%) rapeseed oil, it should be used in ratios of PSP/PSS hardstock:high erucic acid rapeseed oil of from about 20:1 to about 1:1. A food product particularly suitable for utilizing the hardstock of the present invention in combination with the highly hydrogenated high erucic acid rapeseed oil of Example VI is the low-saturate all-purpose shortening of Example VII.

The hardstock of the present invention has been found suitable for use in combination with highly hydrogenated high-erucic acid rapeseed oil type hardstocks because when these high-erucic oils are fully hydrogenated, they become high in behenic acid and high in BSB triglycerides. (B=behenic acid; S=stearic acid.) The beta-prime crystalline morphology and stability of BSB triglycerides (2-stearoyldibehenin) has been identified and discussed by E. S. Lutton and A. J. Fehl in 2-Stearoyldibehenin," *Journal of the American Oil Chemists' Society*, Vol. 49, No. 5, pp. 336–337 (1972), herein incorporated by reference. When the stable beta-prime PSP/PSS hardstock of the present invention is used in combination with high BSB rapeseed oil hardstock in shortening and peanut butter, it should be used in ratios of PSP/PSS hardstock:BSB hardstock of from about 20:1 to about 1:1.

When the beta-prime stable hardstock of the present invention is blended with another beta-prime stable hardstock in a food product, the total hardstock concentration therein can be reduced. Blends of two beta-prime stable triglyceride hardstocks yields fatty food products, especially shortenings, which exhibit superior performance with a minimum concentration of saturated fatty acid groups, particularly that of palmitic acid. This is possible because the incorporation of the beta-prime stable hardstock of the present invention in various food compositions allows a reduction in the amount of intermediate-melting solid fats that need to be included in the composition. Since said intermediate-melting solid fats are generally high in saturated fatty acids, particularly palmitic acid, this results in an overall reduction in saturated fatty acids. The reduction of saturated fatty acids is desirable from a health standpoint.

The beta-prime stable triglyceride hardstock of the present invention is also suitable for use in combination with many classes of non- or partially-digestible fatty materials. "Non-digestible", as used herein, means that substantially all of the material is not digested or absorbed by the body. Said material passes through the digestive system substantially the same as when it was ingested. The term "partially-digestible" means that at least about 30% of the material is not digested or absorbed by the body.

When the beta-prime stable PSP and PSS triglyceride hardstock is used in combination with the non- or partially-digestible fatty material as described herein, it should be used in ratios of PSP/PSS hardstock to non- or partially-digestible fatty material of from about 1:2.9 to about 1:40, preferably from about 1:3.9 to about 1:11.7. When the beta-prime stable hardstock of the present invention is used with non- or partially-digestible fatty materials in formulations which require the incorporation of hardstock material, from about 0% to about 50% of said fatty materials may be a hardstock material.

These non- or partially-digestible fatty materials contain fatty moieties which typically have carbon chain lengths of 8–24 carbon atoms. Examples of such materials include, but are not limited to, those described in the following patents, all incorporated by reference herein: fatty alcohol esters of polycarboxylic acids (U.S. Pat. No. 4,508,746 of Hamm, assigned to CPC International, Inc., issued Apr. 2, 1985); fatty polyesters of polyglycerol (U.S. Pat. No. 3,932,532 of Hunter et al., assigned to ICI United States, Inc., issued Jan. 13, 1976) (food use disclosed in German Patent No. 207,070, issued Feb. 15, 1984)); ethers and ether-esters of polyols containing the neopentyl moiety (U.S. Pat. No. 2,962,419 of Minich, issued Nov. 29, 1960); fatty alcohol diesters of dicarboxylic acids such as malonic and succinic acid (U.S. Pat. No. 4,582,927 of Fulcher, assigned to Frito-Lay, Inc., issued Apr. 5, 1986); triglyceride esters of alpha branched chain-alkyl carboxylic acids (U.S. Pat. No. 3,579,548 of Whyte, assigned to The Procter & Gamble Co., issued May 18, 1971); and sugar and sugar alcohol fatty acid polyesters (U.S. Pat. Nos. 3,600,186 of Mattson and Volpenhein, issued Aug. 17, 1971; 4,005,195 to Jandacek, issued Feb. 12, 1976; 4,005,196 to Jandacek and Mattson, issued Feb. 12, 1976; 4,034,083 to Mattson, issued Nov. 3, 1975; and 4,241,054 to Volpenhein and Jandacek, issued Dec. 8, 1978; all assigned to The Procter & Gamble Company).

Preferred for use in combination with the beta-prime stable hardstock of the present invention are sugar and sugar alcohol fatty acid polyesters. The term "sugar" is used herein in its conventional sense as generic to mono- and disaccharides. The term "sugar alcohol" is likewise used herein in its conventional sense as generic to the reduction product of sugars wherein the aldehyde or ketone group has been reduced to an alcohol.

Examples of suitable monosaccharides are those containing 4 hydroxyl groups such as xylose, arabinose, and ribose; the sugar alcohol derived from xylose, i.e., xylitol, is likewise suitable. The monosaccharide erythrose is not suitable for use in the non- or partially-digestible fatty materials described herein since it only contains 3 hydroxyl groups; however, the sugar alcohol, derived from erythrose, i.e. erythritol, contains 4 hydroxyl groups and is thus suitable. Among 5 hydroxl-containing monosaccharides that are suitable for use herein are glucose, mannose, galactose, fructose, and sorbose. A sugar alcohol derived from sucrose, glucose, or sorbose, e.g., sorbitol, contains 6 hydroxyl groups and is also suitable as the alcohol moiety of the fatty acid ester compound. Examples of suitable disaccharides are maltose, lactose, and sucrose, all of which contain 8 hydroxl groups.

Most preferred for use herein are the sucrose fatty acid polyesters. The sucrose fatty acid polyesters are prepared by a variety of methods known to those skilled in the art. These methods include: transesterification of the sucrose with methyl, ethyl or glycerol fatty acid esters using a variety of catalysts; acylation of the sucrose with fatty acid chlorides; acylation of the sucrose with fatty acid anhydrides; and acylation of the sucrose with fatty acids, per se. Mixtures of different fatty acids are used in the synthesis. The preparation of sucrose fatty acid esters is described in general in U.S. Pat. Nos. 2,831,854 to Tucker and Martin, issued Apr. 22, 1958; 3,963,699 to Rizzi and Taylor, issued June 15, 1976; and 4,517,360 to Volpenhein, issued May 14, 1985; all assigned to The Procter & Gamble Company, and all incorporated by reference herein.

The sucrose fatty acid polyesters most preferred for use herein are substantially nondigestible and nonabsorbable. Therefore, the sucrose esters must have at least four fatty acid ester groups. Sucrose fatty acid ester compounds that contain three or less fatty acid ester groups are digested in, and the products of digestion are absorbed from, the intestinal tract much in the manner of ordinary triglyceride fats, whereas sucrose fatty acid ester compounds that contain four or more fatty acid ester groups are substantially nondigestible and consequently nonabsorbable by the human body. It is not necessary that all of the hydroxyl groups of the sucrose be esterified with fatty acid, but it is preferable that the sucrose contain no more than two unesterified hydroxyl groups. Preferably the sucrose fatty acid esters have: (a) a total content of octa-, hepta-, and hexaesters of not less than 95%; (b) an octa-ester content of not less than 70%; and (c) a content of the penta- and lower esters of not more than 3%.

The fatty acid groups esterified to the sucrose molecule contain from about 2 to about 24 carbon atoms, and preferably from about 14 to about 18 carbon atoms. Examples of such fatty acids include caprylic, capric, lauric, myristic, myristoleic, palmitic, palmitoleic, stearic, oleic, ricinoleic, linoleic, linolenic, eleostearic, arachidic, arachidonic, behenic, and erucic acid. The fatty acids can be derived from naturally occurring or synthetic fatty acids; they can be saturated or unsaturated, including positional and geometrical isomers. The fatty acids esterified to the sucrose molecule are of mixed chain length to obtain the rheology and stability properties required herein.

Exemplary of a noncaloric fat-like material for use in combination with the beta-prime stable hardstock of the present invention is a mixture of the hexa-, hepta-, and octa-esters of sucrose and medium- and long-chain fatty acids obtained from edible fats and oils and/or fatty acid sources that are generally recognized as safe or have been approved for direct food use by U.S. Food and Drug Administration regulations. Fatty acids with chain lengths of 2 to 24 carbon atoms can be used.

A particularly preferred example of the sucrose polyesters preferred for use in combination with the beta-prime stable tailored triglyceride hardstock of the present invention is shown in Example VIII.

A food product wherein the use of a blend of the beta-prime stable hardstock of the present invention and non- or partially-digestible fatty materials is especially preferred is a reduced-calorie shortening. Said shortening could contain as much as 75% by weight of the non- or partially-digestible fatty material. It is preferable to supplement the shortening with vitamin E at a level of 1.0 mg d-alpha-tocopherol equivalents per gram of said fatty material. An example of such a reduced-calorie shortening is disclosed herein at Example VIII.

The beta-prime stable tailored triglyceride hardstock of the present invention is also suitable for use in peanut butter. The incorporation of the hardstock in peanut butter provides a softer peanut butter exhibiting improved storage stability by facilitating more effective entrapment of the liquid oil components. The hardstock of the present invention also yields a peanut butter exhibiting less stickiness in the mouth of the consumer upon ingestion.

The hardstock of the present invention is also suitable for use as a base or a stabilizer in various cosmetic and pharmaceutical products. These products include, but are not limited to, stick-, lotion-, or cream-types and emulsion- and oleo-form products. Oleo-form cosmetic products encompass such items as lipstick, lip cream, stick-pomade, lip gloss, pastille, and deodorant.

The following examples will further clarify the invention described herein. An Analytical Methods section following the examples will describe some of the methods used in generating the data included in the examples.

EXAMPLE I

Hexane Fractionation of Cottonseed Stearine I 100 grams of melted cottonseed stearine was combined with 400 grams hexane and crystallized at approx.

−14° C. for 16 hours. The precipitate was filtered by gravity in an approx. −14° C. environment to prevent the melting of the crystals. The crystals were washed repeatedly with 100 grams of cold hexane (approx. −8° C.). After the washing of the precipitate, the temperature was gradually increased and the initial filtrate after washing was not recovered. After further fractionation, the fraction "E" was the crystalline portion retained on the filter paper. The fraction "B" was the filtrate.

The fractions were collected and dried, removing the hexane in a heated water bath under vacuum. Next, the approximate triglyceride composition of each fraction was determined by GC-CNP* and is shown in Table 1.

*CNP (Carbon Number Profile) is used to identify the triglyceride composition of the structural fat as determined by Gas Chromotography (CNP-GC) or by High Performance Liquid Chromotography (CNP-HPLC). The CNP indicates the percentage of triglycerides having a certain number of carbon atoms for the combined fatty acid residues attached to the glyceride. These methods of determining CNP are explained in part A. of the Analytical Methods section following the examples.

TABLE 1

| CG-CNP | Starting Material | B | E |
|---|---|---|---|
| 32 | 0.5% | 0.5% | 1.5% |
| 34 | 0.2% | 0.2% | 0.2% |
| Total Diglycerides | 0.7% | 0.7% | 1.7% |
| 48 | 4.6% | 1.3% | 11.7% |
| 50 | 80.1% | 92.1% | 80.0% |
| 52 | 8.3% | 3.7% | 3.6% |
| 54 | 5.0% | 1.3% | 0.8% |

As shown in Table 1, the composition of the fraction B has a significantly improved composition over the starting material. It contains an increased concentration (92.1%) of the desirable PUP triglycerides (C50) and a significantly reduced concentration of both undesirable PPP (C48) and UUU (C54) triglycerides. This fraction B, after hydrogenation, should have the preferred hardstock triglyceride (PSP, PSS, PPP, SSS) composition.

The fraction E contains an increased concentration (11.7%) of the undesirable tripalmitin (PPP) and shows no increase in PUP content over the starting material.

EXAMPLE II

Hexane Fractionation of Cottonseed Stearine II 100 grams of melted cottonseed stearine was combined with 300 grams of hexane and crystallized at approx. −18° C. for 16 hours. The precipitate, an intermediate-melting fraction, was filtered by gravity in a −18° C. environment and washed repeatedly with 75 grams of cold hexane (−18° C.). Both the precipitate and the filtrate, a low-melting fraction, were retained and analyzed.

Table 2 illustrates the CNP-GC compositions of the fractions obtained.

Table 2

| CNP-GC | Starting Material | Intermediate Melting Fraction (Precipitate) | Low Melting Fraction (Filtrate) |
|---|---|---|---|
| 32 | 0.5% | 1.0% | 0.3% |
| 34 | 0.5% | 0.6% | 1.3% |
| 36 | 0.4% | 0.1% | 1.7% |
| Total Diglycerides | 1.4% | 1.7% | 3.3% |
| 48 | 1.5% | 1.6% | 1.9% |
| 50 | 69.5% | 87.2% | 29.9% |
| 52 | 15.2% | 6.0% | 33.6% |
| 54 | 10.5% | 2.5% | 23.2% |

The intermediate-melting fraction (precipitate) shows a substantial increase in the desirable PUP fraction (from 69.5% up to 87.2%) and a decrease in the undesirable UUU fraction (from 10.5% down to 2.5%). The concentration of diglycerides is less in the intermediate-melting fraction (1.7%) than in the low-melting fraction (3.3%).

EXAMPLE III

Non-Solvent Fractionation of Cottonseed Oil Stearine 100 pounds of commercial grade hexane fractionated cottonseed oil Stearin ® (manufactured by Ranchers Cotton Oil, P.O. Box 2596, Fresno, Calif. 93745 containing 2.2% tripalmitin is first heated to 4 and then cooled and crystallized at 27° F. in an agitated vessel for 3 hours. The precipitate is filtered under vacuum.

94% of the filtrate recovered contains a reduced tripalmitin concentration (1.2%) according to carbon number profile analysis by High Performance Liquid Chromatography (CNP-HPLC) and carbon number profile analysis by Gas Chromatography (CNP-GC). The 6% precipitate contains 13.7% tripalmitin as measured by CNP-HPLC. The methods used herein are explained in part A. of the Analytical Methods section following the examples.

EXAMPLE IV

Acetone Fractionation or Cottonseed Stearine 400 grams of melted cottonseed stearine was combined with 1500 grams acetone at 55° C. and cooled to 3.3° C. and filtered rapidly at reduced pressure. The precipitate was washed with cold acetone (0° C.) and dried in a vacuum oven (C-2). The filtrate was cooled and crystallized at 0° C. for 3 hours. The precipitate (C-3) was vacuum filtered and washed with cold acetone 0° C. and dried. The filtrate was cooled to −12° C. for approximately 1 hour. The new precipitate (C-4) was filtered and washed with cold acetone and dried under vacuum. The filtrate was cooled to −13° C. for 2½ hours but no precipitate was formed. The filtrate was heated in a water bath and the acetone was evaporated under vacuum and identified as C-5.

In Table 3 below, the carbon number profile analysis by Gas Chromotography (CNP-GC) clearly indicates that the C-3 middle fraction concentrates the desirable PUP (C50) component (from 54.9% up to 88.5%) and reduces the undesirable diglyceride content (from 3.5% down to 2.1%) and the UUU content (from 14.0% to down 0.9%).

TABLE 3

| CNP-GC | Starting Material | C-2 | C-3 | C-4 | C-5 |
|---|---|---|---|---|---|
| C32 | 1.0% | 1.0% | 1.2% | 3.2% | 0.5% |
| C34 | 1.3% | 0.5% | 0.6% | 1.0% | 2.6% |
| C36 | 1.2% | 0.2% | 0.3% | 0.5% | 3.0% |
| Total Diglycerides | 3.5% | 2.7% | 2.1% | 4.7% | 6.1% |
| C46 | 0.2% | 0.4% | 0.2% | 0.3% | 0.1% |
| C48 | 2.0% | 4.2% | 2.0% | 2.2% | 1.7% |
| C50 | 54.9% | 87.1% | 88.5% | 64.1% | 7.9% |
| C52 | 21.2% | 4.1% | 4.8% | 19.4% | 41.4% |
| C54 | 14.0% | 0.9% | 0.9% | 4.9% | 34.1% |
| C56 | 1.5% | 0.2% | 0.1% | 1.1% | 3.2% |
| C58 | 0.2% | — | — | 0.5% | 0.4% |
| C60 | — | — | — | 0.2% | 0.1% |

EXAMPLE V

Hydrogenation of Fractionated Palm Oil 360 pounds of commercially available fractionated palm oil known as Chocomate 1000® (previously available and marketed as Chovetta®, manufactured by Intercontinental Speciality Fats SDN.BHD., an Associate Company of Lam Malaysia & Walter Rau, W. Germany, P.O. Box 207, Port Kelang, Selangof, Malaysia) was hydrogenated in a standard pilot plant unit until the R.I.* dropped from 35.9 to 31.2. During the process, the pressure was gradually increased (e.g., from atmospheric pressure to 110 psig). 1300 grams of fresh standard nickel catalyst was used. The hydrogenation was completed in five hours at 450° F. (435° F. with maximum 470° F.). Table 4 below shows the relevant GCFAC values and I.V.* values.

*R.I. (Refractive Index) is conducted at 60° C. (Butyro Scale). Variations in the R.I. of fats, along with variations in other optical properties of fats, can indicate the structure and compositions of fatty acids and glycerides. Here the drop in R.I. signifies a decrease in the unsaturation of the fatty acids during hydrogenation.

TABLE 4

| | GCFAC Values | |
|---|---|---|
| Fatty Acid | Before Hydrogenation | After Hydrogenation |
| 12 | 0.3% | 0.3% |
| 14 | 0.9% | 0.9% |
| 16 | 54.4% | 53.3% |
| 18 | 6.2% | 44.3% |
| 18:1 | 3.3% | 0.1% |
| 18:2 | 0.5% | — |
| 20:0 | 0.5% | 0.6% |
| I.V. | 35.0 | 0.3 |

Table 5 below shows Argentation Values**** and Table 6 below shows CNP-GC values for triglycerides present in the sample.

**** Argentation values represent the triglyceride composition in terms of positional isomers as determined by Argentation thin layer chromatography (hereinafter Argentation). Argentation uses silver nitrate as a complexing reagent in a chromatographic separation. The triglycerides separate according to the degree of unsaturation and the position of the fatty acid on the triglyceride molecule. However, chain length of the saturated fatty acids cannot be determined by this method. The specific Argentation method used to determine the triglyceride composition of the structural fat of the present application is described in Section C. of the Analytical Methods section following the examples.

TABLE 5

| Argentation Values | |
|---|---|
| Triglyceride | % |
| SSS | 3.9 |
| SES | 0.2 |
| SOS | 71.2 |
| SSO | 6.2 |
| SLS | 6.9 |
| SOO | 6.7 |
| SLO | 2.1 |
| OOO | 0.6 |

S = saturated fatty acid;
O = oleic acid;
E = elaidic acid;
L = linoleic acid

TABLE 6

| CNP-GC Values | |
|---|---|
| Glycerides | CNP-GC |
| Diglycerides | 1.0 |
| 48 | 3.9 |
| 50 | 69.3 |
| 52 | 19.3 |
| 54 | 3.7 |

EXAMPLE VI

Hydrogenation of High Erucic Acid Rapeseed (HEAR*) Oil

Refined and Bleached HEAR oil was hydrogenated by the same process as shown in Example V, except that the Initial R.I. equals 49.0, and the Final R.I. equals 34.8. This created a high beneic acid hardstock.

*HEAR oil as used herein represents a commercial oil manufactured by Humko Products, Memphis, Tenn. 38101.

Table 7 below represents the composition of the HEAR oil before and after hydrogenation as determined by GCFAC:

TABLE 7

| | GCFAC | |
|---|---|---|
| Carbon Number of Fatty Acids | Before Hydrogenation | After Hydrogenation |
| 16:0 | 3.1 | 3.6 |
| 18:0 | 1.1 | 39.6 |
| 18:1 | 13.0 | 0 |
| 18:2 | 14.8 | 0 |
| 18:3 | 9.9 | 0 |
| 20:0 | 0.7 | 8.2 |
| 22:0 | 0.7 | 47.1 |
| 24:0 | 0.3 | 1.4 |
| 20:1 | 6.7 | 0 |
| 22:1 | 45.6 | 0 |
| 24:1 | 1.2 | 0 |

EXAMPLE VII

Low Saturate All-Purpose Shortening 2000 grams fat blend having the following formulation was made:

Formulation

| | Formulation | |
|---|---|---|
| | Component | Weight Percent |
| 1. | PSP/PSS Hardstock | 8 |
| 2. | High behenic (45%) hardstock | 1.1 |
| 3. | Lightly hydrogenated canola oil (I.V. = 94) | 87.4 |
| 4. | Dimoden-O^R (distilled mono and di-glycerides) | 1.5 |
| 5. | Hydrogenated palm/soybean blend 70/30 (I.V. = 43) | 2.0 |

Components

PSP/PSS hardstock (Component #1) is that described in Example V.

High benehic hardstock (Component #2) is that described in Example VI.

Dimodan-O ® (Component #4) is manufactured by Grinsted Products, Inc., P.O. Box 26, 201 Industrial Parkway, Airport, Kan. 66031.

Preparation 500 grams of the above oil blend was added to each of four pre-chilled 9×13" glass dishes, each in a plastic bag, in a dry ice chest. The mixtures were allowed to freeze rapidly for minutes (in order to maximize small crystals) and were then removed to a 15.6° C. environment for 1½ hours. The material in the four dishes was next combined and transferred at approx. 10° C. into a Cuisinart (DLC7 Super Pro) mixer and then mixed and scraped repeatedly at approx. 24° C. until a smooth consistency was achieved. The percent air of the mixtures was then adjusted to the desired level by using vacuum to deaerate if needed. The resulting shortening was tempered at 29.5° C. for 48 hours.

The low-saturate all purpose shortening exhibited good creaming properties and good heat stability to 37.8° C.. This shortening retained its plasticity after extensive temperature cycling.

EXAMPLE VIII

A Reduced-Calorie Shortening made with a Non-Digestible Fatty Material

Formulation

| | Component | Formulation Weight Percent |
|---|---|---|
| 1. | Liquid triglyceride, partially hydrogenated to I.V. of 107 | 53.5 |
| 2. | Intermediate Melting triglyceride hardened to I.V. of 43 | 3.5 |
| 3. | High PSP/PSS palm hardstock | 3.5 |
| 4. | Emulsifier | 4.5 |
| 5. | Intermediate melting sucrose polyester | 29.7 |
| 6. | Hardstock sucrose polyester | 5.3 |

Components

The liquid triglyceride (Component #1) is soybean oil which has been partially hydrogenated to I.V. of 107.

The Intermediate Melting triglyceride (Component #2) is a 70/30 blend of palm/soybean oil which has been hydrogenated to I.V. of 43.

The High PSP/PSS containing palm hardstock (Component #3) is prepared as described in Example V.

The emulsifier (Component #4) is partially hydrogenated soybean oil, mono- and diglycerides.

Shown below in Table 8 are the intermediate melting sucrose polyester (Component #5) and hardstock sucrose polyester (Component #6):

TABLE 8

| | Intermediate Melting Sucrose Polyesters (Component #5) | Hardstock Sucrose Polyesters (Component #6) |
|---|---|---|
| Ester Distribution | | |
| Octa | 77.8 | 96.1 |
| Hepta | 22.0 | 3.9 |
| Hexa | 0.2 | <0.1 |
| Penta and lower | <0.1 | <0.1 |
| Solid Fat Content | | |
| 21° C. | 53.3 | 85.5 |
| 37.8° C. | 17.7 | — |
| 40.5° C. | 10.9 | 79.1 |
| GCFAC | | |
| C-16 | 11.5 | 9.7 |
| C-18 | 54.8 | 87.8 |
| C-18:1 | 17.9 | 1.0 |
| C-18:2 | 14.0 | 0.3 |
| C-18:3 | 0.8 | — |
| C-20 | 0.5 | 0.6 |
| C-22 | 0.3 | 0.2 |
| I.V. | 41.8 | 1.5 |
| Viscosity @ 10 sec$^{-1}$ @ t = 10 min (Poise) | 142 | N/A |
| Liquid/solid stability @ 486,000 g @ 1 hr | 92 | N/A |

The intermediate melting sucrose polyesters suitable for use herein may be prepared by this specific, but non-limiting example: sucrose is esterified with methyl esters of a fully hydrogenated soy oil (I.V.=8) and a partially hydrogenated soy oil (I.V.=107), blended in about a 55:45 ratio.

The intermediate melting sucrose fatty acid esters, at 37.8° C., have a non-Newtonian plastic rheology, in particular a viscosity of at least about 0.5 poise, more preferably at least about 5 poise, more preferably at least about 10 poise, and most preferably at least about 15 poise, after 10 minutes of steady shear at 10 sec.$^{-1}$ Viscosity and yield stress are known rheological properties, and can be measured by use of an instrument such as a plate and cone viscometer (e.g., a Ferranti-Shirley viscometer, manufactured by Ferranti Electric, Inc., 87 Modular Ave., Commack, N.Y. 11725). The basics of rheology are discussed in Idson, "Rheology: Fundamental Concepts", Cosmetics and Toiletries, Vol. 93, pp. 23–30 (July 1978). Viscosity is calculated from a point on the rheogram curve. Additional details are provided below in Section F. of the Analytical Methods section.

The intermediate melting sucrose esters also have a liquid/solid stability of at least about 30%, preferably at least about 50%, more preferably at least about 70%, and most preferably at least about 90% at 37.8° C. By "liquid/solid stability" as used herein is meant that the liquid portion of the polyesters does not readily separate from the solid portion. In general terms, the esters can be described as being very viscous and plastic. See Section G. of the Analytical Methods Section for a detailed description of the liquid/solid stability measurement.

These polyesters preferably have, at 37.8° C., a Solid Fat Content (SFC) value of at least about 5%, more preferably at least about 10%. The SFC provides a reasonable approximation of the percent by weight solids of a particular fatty material at a given temperature. The method of measuring the SFC in polyol fatty acid polyesters is set forth in Section D. of the Analytical Methods section.

It was discovered that intermediate melting sucrose fatty acid esters having the above-mentioned rheology and liquid/solid stability are effective at avoiding anal leakage while containing surprisingly low levels of solids at body temperature. The low solids levels allow the production of non-waxy, excellent tasting foods. For further details on esters having these rheology characteristics, see European Patent Application No. 236,288 of Bernhardt, published Sept. 9, 1987, incorporated by reference herein.

The intermediate melting sucrose fatty acid esters can be a single type of ester or a mixture of esters. It is not critical that each type of ester has the above-mentioned physical properties as long as the intermediate melting sucrose esters as a whole have these physical properties.

Hardstock sucrose polyesters suitable for use herein are selected from hardstock sugar fatty acid esters, and mixtures thereof, and it has an iodine value of not more than about 12. The hardstock contains between about 75% and about 100% solids when measured at body temperature.

As discussed more fully below, it has been found that in order to achieve the most rapid crystallization of the intermediate melting sucrose fatty acid ester compositions from the melted state, the average fatty acid chain length of the hardstock material fatty acids must be not less than about the average fatty acid chain length of the intermediate melting sucrose ester fatty acids. However, crystallization more rapid than that of the sucrose esters alone can be achieved using hardstock materials with a shorter average fatty acid chain length as well.

The hardstock is a substantially completely hydrogenated sugar fatty acid ester having an iodine value not exceeding about 12.

The sucrose fatty acid polyesters are those described generally above. However, the hardstock sucrose polyesters generally contain fatty acids that are more saturated than unsaturated, and more longer than shorter fatty acid chains. Typical examples of hardstock polyol polyesters include completely esterified sucrose polyester made from the esters of hardened palm or soybean oils, sucrose heptastearate, xylitol pentastearate, galactose pentapalmitate, and the like, or mixtures thereof.

Additional details are provided herein immediately below under the Preparation section and in the Analytical Methods section at the conclusion of the examples.

Preparation

The shortening product having the formulation and components described above is produced using standard shortening equipment such as a scraped surface heat exchanger followed by mechanical agitation and tempering. Processing temperatures and pressures can be optimized for the specific equipment used.

The penetration of the shortening is about 175 millimeters/10. The appearance is creamy and smooth.

The reduced calorie shortenings made with the non- or reduced-calorie fatty materials as disclosed herein possess a particular Solid Fat Content curve and particular penetration properties and thereby exhibit increased smoothness and decreased graininess.

The Solid Fat Content value (SFC) provides a reasonable approximation of the percent by weight solids of a particular fatty material at a given temperature. The method for determining SFC is described in Part D. of the Analytical Methods section following the Examples.

The reduced calorie shortenings described herein exhibit a relatively flat Solid Fat Content (SFC) slope (SFC vs. temperature) for the shortenings, relative to processing and usage temperatures. Specifically, the level of solids at temperatures encountered during the processing, packing, warehousing, shipping, and subsequent consumer storage conditions must be relatively flat. If the solids profile is not relatively flat across this temperature range, the finished product will melt and recrystallize in moving across this temperature range and will be brittle, chunky, or in other ways not smooth and creamy in appearance. The temperature range of 10° C. to 41° C. is representative of the temperature range a shortening product would encounter during processing, packing, warehousing, shipping, and subsequent consumer storage. The method for measuring penetration is described in Part E. of the Analytical Methods section following the Examples.

The penetration or firmness of the shortening at 21° C. is also critical to providing a creamy appearance. The reduced-calorie shortening has a penetration between about 120 millimeters/10 and about 400 millimeters/10 at 21° C. Preferably, the reduced-calorie shortening has a penetration between about 150 millimeters/10 and about 250 millimeters/10 at 21° C.

EXAMPLE IX

Peanut Butter Containing Beta-Prime Stable Hardstock Stabilizer

Formulation

| EXAMPLE IX Peanut Butter Containing Beta-Prime Stable Hardstock Stabilizer Formulation | |
|---|---|
| Ingredients | Weight Percent |
| Peanut paste | 90.0 |
| Salt | 1.2 |
| Sucrose | 5.8 |
| Molasses | 0.5 |
| Soybean monoglycerides | 0.7 |
| Beta-Prime Stable Hardstock Stabilizer* | 1.2 |
| Peanut Oil | .6 |

*The Beta-Prime Stable hardstock stabilizer contains 79% fully hydrogenated PSP as prepared in Example V (I.V. < 1.0) and 21% fully hydrogenated high behenic (45%) rapeseed oil as prepared in Example VI (I.V. < 1.0).

Preparation

The Beta-Prime Stable Hardstock stabilizer is mixed with other minor ingredients (soybean monoglycerides, molasses, peanut oil) and fully melted over a steam bath.

The peanuts for this product are prepared utilizing methods used in conventional peanut butter processing. The peanuts are dry roasted in a continuous roaster. After ambient air cooling the peanuts are blanched and sorted. Next, the peanuts are finely ground into a mix tank where the melted minors, along with other seasoning agents (salt, sucrose) are added. After approximately 30 minutes mix time, the product is homogenized and pumped through a standard crystal nucleating freezing step. Finally, following a crystal growth step, the product is packed into jars and sealed.

This peanut butter has excellent texture and exhibits enhanced storage stability because the Beta-Prime Stable Hardstock Stabilizer of the present invention incorporated therein increases the entrapment of liquid oil components.

ANALYTICAL METHODS

A

1. CNP-GC Method

The carbon number profile (CNP) of triglycerides of the hardstock of the present invention can be determined by programmed temperature-gas chromatography (GC) using a short fused silica column coated with methyl silicone for analysis and characterization of the composition by molecular weight. The glycerides are separated according to their respective carbon numbers, wherein the carbon number defines the total number of carbon atoms on the combined fatty acid residues. The carbon atoms on the glycerol molecule are not counted. Glycerides with the same carbon number will elute as the same peak. For example, a triglyceride composed of three C16 (palmitic) fatty acid residues will co-elute with triglycerides made up of one C14 (myristic), one C16 and one C18 (stearic) fatty acid residue or with a triglyceride composed of two C14 fatty acid residues and one C20 (arachidic) fatty acid residue.

Preparation of the fat sample for analysis is as follows: 1.0 milliliter of a tricaprin internal standard solution (2 micrograms/milliliter) is pipetted into a vial. The methylene chloride solvent in the standard solution is evaporated using a steam bath under a nitrogen stream. Two drops of the fat sample (20 to 40 micrograms) are pipetted into a vial. If the fat sample is solid, it is melted on a steam bath and stirred well to insure a representative sample. 1.0 milliliter of bis (trimethylsilytrifluoroacetamide) (BSTFA) is pipetted into the vial which is then capped. The contents of the vial are shaken vigorously and then placed in a beating block (temperature of 100° C.) for about 5 minutes.

For determining the CNP-GC of the prepared fat samples, a Hewlett-Packard 5880A series gas chromatograph equipped with temperature programming and a hydrogen flame ionization detector is used together with a Hewlett-Packard 3351B data system. A 2 meters long, 0.22 millimeters diameter fused silica capillary column coated with a thin layer of methyl silicone (Chrompak CP-SIL 5) is also used. The column is heated in an oven where temperature can be controlled and increased according to a specified pattern by the temperature programmer. The hydrogen flame ionization detector is attached to the outlet port of the column. The signal generated by the detector is amplified by an electrometer into a working input signal for the data system and recorder. The recorder prints out the gas chromatograph curve and the data system electronically integrates the area under the curve. The following instrument conditions are used with the gas chromatograph:

| | |
|---|---|
| Septum purge | 1 milliliter/minute |
| Inlet pressure | 5 pounds per square inch |
| Vent flow | 75 milliliters/minute |
| Makeup carrier | 30 milliliters/minute |
| Hydrogen | 30 milliliters/minute |
| Air | 400 milliliters/minute |

1.0 microliter of the prepared fat sample is taken by a gas-tight syringe and injected into the sample port of the gas chromatograph. The components in the sample port are warmed up to a temperature of 365° C. and swept by a helium carrier gas to push the components into the column. The column temperature is initially set at 175° C. and held at this temperature for 0.5 minutes. The column is then heated up to a final temperature of 355° C. at a rate of 25° C./minute. The column is maintained at the final temperature of 355° C. for an additional 2 minutes.

The chromatographic peaks generated are then identified and the peak areas measured. Peak identification is accomplished by comparison to known pure glycerides previously programmed into the data system. The peak area as determined by the data system is used to calculate the percentage of glycerides having a particular Carbon Number ($C_N$) according to the following equation:

$$\% \ C_N = (\text{Area of } C_N / S) \times 100$$

wherein S = sum of Area of $C_N$ for all peaks generated.

The Area of $C_N$ is based upon the actual response generated by the chromatograph multiplied by a response factor for glycerides of the particular Carbon Number. These response factors are determined by comparing the actual responses of a mixture of pure glycerides of various Carbon Numbers to the known amounts of each glyceride in the mixture. A glyceride generating an actual response greater than its actual amount has a response factor less than 1.0; likewise, a glyceride generating a response less than that of its actual amount has a response factor of greater than 1.0. The mixture of glycerides used (in a methylene chloride solution) is as follows:

| Component | Carbon No. | Amount (milligrams/milliliters) |
|---|---|---|
| Palmitic acid | 16 | 0.5 |
| Monopalmitin | 16 | 0.5 |
| Monostearin | 18 | 0.5 |
| Dipalmitin | 32 | 0.5 |
| Palmitostearin | 34 | 0.5 |
| Distearin | 36 | 0.5 |
| Tripalmitin | 48 | 1.5 |
| Dipalmitostearin | 50 | 1.5 |
| Distearopalmitin | 52 | 1.5 |
| Tristearin | 54 | 1.5 |

2. CNP-HPLC Method

The carbon number profile (CNP) of the triglycerides of the hardstock of the present invention is also measured by high performance liquid chromatography (HPLC). The method measures the percentages of medium chain triglycerides, mono-long chain, and di-long chain triglycerides. A triglyceride sample to be analyzed is injected on a reverse phase liquid chromatograph (LC) equipped with a mass (evaporative light scattering) detector. A linear gradient of increasing methylene chloride in acetonitrile is used to separate all of the triglycerides based on fatty acid chain length. Retention time increases with increasing fatty acid chain length. Thus, medium chain triglycerides are eluted first, followed by mono-long chain and then di-long chain triglycerides.

Apparatus

| Apparatus | |
|---|---|
| Dispensers | 1 milliliter, American Scientific #P4952-1, or equivalent, American Scientific Products, 1430 Waukegan Rd., McGaw Park, IL 60085 |
| Pasteur pipets, glass | Fisher #13-678-7A, or equivalent, Fisher Scientific Co., 203 Fisher Bldg., Pittsburgh, PA 15219 |
| Vials, glass | 2 dram with foil-lined cap |
| Autosampler vials | 2 milliliter, Fisher #03-340-SG, Fisher Scientific Co. |
| Vial caps | PTFE Rubber, Fisher #03-340-13C, Fisher Scientific Co. |
| LC columns | 2 Beckman Ultrasphere ODS, 5 micrometers, 0.46 centimeter inner diameter × 25 centimeters, Beckman Instruments, Inc., 2500-T Harbor Blvd., Fullerton, CA 92634 |
| LC system | Hewlett-Packard 1090L with Ternary DR5 pump, variable volume injector, autosampler, heated column compartment and column switching valve, Hewlett-Packard Co., Scientific Instruments Div., 1601-T California Ave., Palo Alto, CA 94304 |
| Mass detector | Applied Chromatography Systems #750/14, Varex Corp., 12221 Parklane Dr., Rockville, MD 20852 |
| Recorder | Kipp & Zonen #BD40, or equivalent, Kipp & Zonen, Div. of Enraf-Nonius, 390-T Central Ave., Bohemia, NY 11716 |
| Laboratory | Hewlett-Packard 3357, or |

-continued

| Apparatus | |
|---|---|
| Automation System (LAS) | equivalent, Hewlett-Packard Co., Scientific Instruments Div. |
| Filters | Gelman #4451, 0.2 μm, or equivalent, Gelman Instrument Co., 605-T S. Wagner Rd., Ann Arbor, MI 48106 |
| Solvent Clarification kit | Waters #85124, Waters Instruments, Inc., 2411-T 7th St. N.W., Rochester, MN 55901 |
| Syringe | 5 milliliters, disposable, Fisher #14-823-200, or equivalent, Fisher Scientific Co. |

Reagents

| Reagents | |
|---|---|
| Methylene chloride | Burdick and Jackson, UV Grade, American Scientific #300-4L, American Scientific Products |
| Acetonitrile | Burdick and Jackson, UV Grade, American Scientific #015-4L, American Scientific Products |

Sample Preparation

1. Weigh 0.1 gram of the melted sample into a 2 dram vial.
2. Dispense 1 milliliter of methylene chloride into vial and mix thoroughly.
3. Filter the sample solution through a 0.2 micrometer filter into an autosampler vial.

LAS Method and Sequence Preparation

1. Set up the integration method, referring to the HP-3357 Quick Reference Guide for instructions. The calibration table is shown in Table 9.
2. Set up a LAS sample sequence for the appropriate number of examples. Refer to the Reference Guide as necessary.

TABLE 9

| | | Calibration Table | | |
|---|---|---|---|---|
| | Time | Factor | Amount | Peak Name |
| 1. | 3.48 | 1.000000 | 1.000000 | C22 |
| 2. | 3.80 | 1.000000 | 1.000000 | C24 |
| 3. | 4.18 | 1.000000 | 1.000000 | C26 |
| 4. | 4.30 | 1.000000 | 1.000000 | C28 |
| 5. | 4.65 | 1.000000 | 1.000000 | C30 |
| 6. | 5.32 | 1.000000 | 1.000000 | C32 |
| 7. | 6.01 | 1.000000 | 1.000000 | C34 |
| 8. | 6.80 | 1.000000 | 1.000000 | C36 |
| 9. | 7.87 | 1.000000 | 1.000000 | C38 |
| 10. | 8.98 | 1.000000 | 1.000000 | C40 |
| 11. | 10.31 | 1.000000 | 1.000000 | C42 |
| 12. | 11.88 | 1.000000 | 1.000000 | C44 |
| 13. | 13.49 | 1.000000 | 1.000000 | C46 |
| 14. | 15.35 | 1.000000 | 1.000000 | C48 |
| 15. | 17.28 | 1.000000 | 1.000000 | C50 |
| 16. | 19.49 | 1.000000 | 1.000000 | C52 |
| 17. | 21.60 | 1.000000 | 1.000000 | C54 |
| 18. | 23.87 | 1.000000 | 1.000000 | C56 |
| 19. | 26.18 | 1.000000 | 1.000000 | C58 |
| 20. | 28.50 | 1.000000 | 1.000000 | C60 |
| 21. | 30.77 | 1.000000 | 1.000000 | C62 |
| 22. | 33.03 | 1.000000 | 1.000000 | C64 |
| 23. | 35.24 | 1.000000 | 1.000000 | C66 |

LC Operation (A) Start-up (1) Turn on power for the HP1090.
(2) Filter all solvents with filtration apparatus.
(3) Fill reservoirs with filtered solvent; reservoir A contains acetonitrile and reservoir B contains methylene chloride. Open helium toggle valve on back of LC and degas solvents for at least 5–10 minutes. Close helium toggle valve.
(4) Set the mass detector to the following settings:
   Attenutation: 2
   Photomultiplier: 2
   Time Constant: 5
   Evaporator Setting: 50
   Nitrogen: 12 pounds per square inch
(5) Set up the mobile phase gradient method in Table 10 on the HP1090 as necessary. Refer to HP1090 Operator's Handbook for programming directions. Once the method is programmed, it will remain in the memory until it is erased, even with power off or instrument unplugged.

TABLE 10

| Mobile Phase Gradient Program |
|---|
| METHOD 1 |
| TMCT |
| SDS CONFIG A = 1 B = 1 C = 0 |
| FLOW = 2 |
| %B = 35 C = 0 |
| OVEN = 40 INJ VOL = 10 SLOWDOWN = 5 |
| MAX PRESS = 300 |
| MIN PRESS = 0 |
| STOP TIME = 40.1 |
| POST TIME = 5 |
| COLUMN SWITCH = 0 |
| E = 0 0 0 0 |
| AT 0 E4 = 1 |
| AT 0 %B = 35 %c = 0 |
| AT .1 E4 = 0 |
| AT 40 %B = 55 %C = 0 |

(B) Autosampler Operation
(1) Place the filled autosampler vials in autosampler holders starting with space "0". Autosampler starts numbering with "0" and the LAS starts numbering with "1", thus the sequence numbers are shifted by one.
(2) Program and start the autosampler for number of injections, refer to handbook.

Reference Standards

A reference standard is used to insure proper LC/detector operation and to verify the identification of the triglyceride peaks. Typically, a well-characterized material is used. When such material is not available, a commercial material such as Nu Chek Prep 50A and 51A can be substituted (Nu Chek Prep, Inc., P.O. Box 172, Elysian, Minn. 56028). The reference standard is analyzed each day prior to sample analyses.

Results

1. As each sample is analyzed, the LAS will generate a report according to the instructions of the integration method. The report lists peak number, retention time, and area percent for a given carbon number of the triglyceride sample.
2. Since retention times of peaks will shift as a function of column usage, verify the proper identification of the reference standards peaks. If peaks are mislabelled, modify the retention time table of the integration method and reanalyze the sequence to generate the new reports.

3. A chromatogram is often helpful to understand the data. Use CPLOT to generate a chromatogram.

B. Fatty Acid Composition (GCFAC Values) Principle

The fatty acid composition of the triglycerides of the beta-prime stable hardstock and of the intermediate melting sucrose fatty acid polyesters and sucrose fatty acid polyester hardstocks of the present invention is measured by gas chromatography. First, fatty acid ethyl esters of the hardstock triglycerides or of the intermediate melting sucrose polyesters and sucrose polyester hardstocks are prepared by any standard method (e.g., by transesterification using sodium ethoxide), and then separated on a capillary column which is coated with DB-WAX stationary phase. The fatty acid ethyl esters are next separated by chain length and degree of unsaturation. A split injection is made with flame ionization detection. Quantitation is performed by an area normalization method. This method can separate fatty acid ethyl esters from C6 to C24.

Equipment

| Equipment | |
|---|---|
| Gas Chromatograph | Hewlett-Packard 5890, or equivalent, equipped with a split injector and flame ionization detector. Hewlett-Packard Co., Scientific Instruments Div., 1601-T California Ave., Palo Alto, CA 94304 |
| Injector | Autosampler Hewlett-Packard 7673A, or equivalent |
| Column | 15 meters × 0.25 millimeter inner diameter, fused silica capillary column coated with DB-WAX (0.25 micron film thickness), Hewlett-Packard Co., Scientific Instruments Div. |
| Data System | Hewlett-Packard 3350, 3000-T Hanover St., Palo Alto, CA 94304 |
| Recorder | Kipp & Zonen, BD40, Kipp & Zonen |

Reference Standards

Two reference standards are used each day of operation to verify proper operation of this method. (1) A reference mixture of fatty acid methyl esters (FAME) is used to check the operation of the instrument. This reference mixture has the following fatty acid composition: 1% $C_{10:0}$, 4% $C_{16:0}$, 3% $C_{18:0}$, 45% $C_{18:1}$, 15% $C_{18:2}$, 3% $C_{18:3}$, 3% $C_{20:0}$, 3% $C_{22:0}$, 20% $C_{22:1}$, and 3% $C_{24:0}$. (2) A reference standard of a commercial shortening is used to check the operation of the total system—ethylation and gas chromatographic analysis. The shortening reference standard has the following fatty acid composition: 0.4% $C_{14:0}$, 21.4% $C_{16:0}$, 9.2% $C_{18:0}$, 40.3% $C_{18:1}$, 23.0% $C_{18:2}$, 2.2% $C_{18:3}$, 0.4% $C_{20:0}$, 1.3% $C_{20:1}$, and 0.3% $C_{22:0}$.

The reference mixture of FAME should be diluted with hexane and then injected into the instrument. A new vial of FAME reference mixture should be opened every day since the highly unsaturated components, $C_{18:2}$ and $C_{18:3}$, oxidize easily. The shortening reference standards should be ethylated with the samples prior to their analysis by capillary gas chromatography. The results from the reference standards should be compared with the known values and a judgment made concerning the completed analysis. If the results of the reference standards are equal to or within ±2 standard deviations of the known values, then the equipment, reagents and operations are performing satisfactorily.

Internal Standards

A reference standard of a known triglyceride is used when determining the fatty acid composition of the hardstock triglycerides or of the intermediate melting sucrose fatty acid polyesters or sucrose fatty acid polyester hardstocks herein. The triglyceride reference standard has the following fatty acid composition: 0.4% $C_{16}$, 21.4% $C_{16}$, 9.2% $C_{18}$, 40.3% $C_{18:1}$, 23.0% $C_{18:2}$, 0.4% $C_{20}$, 1.3% $C_{20:1}$, 2.2% $C_{18:3}$, and 0.3% $C_{22}$.

1. Instrumental Set-up a. Install the column in the gas chromatograph, and set up the instrumental conditions as defined immediately below under Instrumental Conditions.

b. Set up the data system with the appropriate method to acquire and analyze the data. The retention times may have to be adjusted in the method due to instrument variations. Consult the data system reference manual on how to do this—HP3350 User's Reference Manual. Unity response factors are used for each component.

| INSTRUMENTAL CONDITIONS | |
|---|---|
| Instrument | Hewlett-Packard 5890 |
| Column | 15 meters × 0.25 millimeter inner diameter I.D., coated with DB-WAX, 0.25 micron film thickness |
| Column head pressure | 12.5 pounds per square inch |
| Carrier gas | Helium |
| Injector "A" temperature | 210° C. |
| Split vent flow | 100 milliliters/minute |
| Septum purge | 1.5 milliliters/minute |
| Oven temperature profile: | |
| Initial temperature | 110° C. |
| Initial time | 1 minute |
| Rate 1 | 15° C./minute |
| Final temp 1 | 170° C. |
| Final time 1 | 0 minute |
| Rate 2 | 0° C./minute |
| Final temp 2 | 200° C. |
| Final time 2 | 0 minute |
| Rate 3 | 10° C./minute |
| Final temp 3 | 220° C. |
| Final time 3 | 8 minute |
| Detector | FID |
| Detector temp | 230° C. |
| Make-up gas | 42 milliliters/minute |
| Detector $H_2$ flow | 30 milliliters/minute |
| Detector air flow | 300 milliliters/minute |

2. Analysis of Samples—(The samples are analyzed with an area normalization procedure.)

a. Prepare fatty acid methyl esters of the reference standards and triglycerides of the hardstock of the present invention and the intermediate melting sucrose polyester or sucrose polyester hardstock samples according to any standard method.

b. Set up a sequence in the LAS data system to inject the samples and reference standard.

c. Activate the autosampler to inject 1.0 microliter of the samples and standard in the sequence. The gas chromatograph will automatically begin its temperature program and the data system will collect and analyze the data for the sequence.

C. Argentation

The positional isomer triglyceride composition of a fat can be determined by Argentation Thin Layer Chromatography. 20 centimeters square, 250 micron layer thickness, silica gel H plates (Analtech, Newark, Del.) are sprayed with a 2.5% solution of silver nitrate until evenly wet. These plates are then activated in a forced-air oven for 60 minutes at 115° C. and stored in a dark enclosure until cool.

Solutions of the individual fat samples are generated at two concentrations (in chloroform): dilute (5.0 milligrams/milliliter) to better quantitate the major glyceride components and concentrated (50 milligrams/milliliter) to better quantitate the trace components. Analytical standard solutions are prepared for spotting alongside the fat samples of interest. Samples of each individual fat solution are then spotted at 10 micrograms and 100 micrograms concentrations alongside analytical standards which are spotted at 1, 2, 4 and 8 micrograms for each component. A secondary standard of African cocoa butter at concentrations the same as the fat solution is also spotted. After the spotting solution solvent (chloroform) evaporates, the plates are ready for development.

Each analytical plate is developed at room temperature in a darkened chamber with 85% methylene chloride, 15% toluene, 0.1% acetic acid developing solvent until the solvent reaches a prescribed line (17 centimeters from the origin). The developing solvent is allowed to evaporate in a forced nitrogen chamber for 10 minutes.

Each plate is then sprayed evenly with a 25% sulfuric acid solution and placed on a 21 centimeters square by 0.3 centimeter thick aluminum plate stop a hot plate. The plate is heated from 25° C. to 230° C. over a period of 105 minutes.

After cooling to room temperature, the individual fat sample is then quantitatively scanned versus the spotted standards in a Camag densitometer set at 600 nm. The individual scans are integrated by a Spectraphysics SP-4100 integrator and calibration curves are prepared from the spotted standards for quantitation purposes. At least 4 (usually 6) samples for each fat are used to determine the mean levels.

D. Solid Fat Content

The method for determining Solid Fat Content (SFC) values of a fat or shortening by PMR is described in Madison and Hill, *J. Amer. Oil, Chem. Soc.*, Vol. 55 (1978), pp. 328-31 (herein incorporated by reference). Before determining SFC values, the fat or shortening sample is heated to a temperature of 60° C. for at least 0.5 hours or until the sample is completely melted. The melted sample is then tempered at a temperature of 0° C. for 15 minutes, 27° C. for 30 minutes, and 0° C. for 15 minutes. After tempering, the SFC value of the shortening sample at temperatures of 10° C., 21° C., 27° C., 33° C. and 41° C. is determined by pulsed magnetic resonance (PMR) after equilibrating for 30 minutes at each temperature. After tempering, the SFC value of the fat sample at temperature of 10° C., 21° C., 27° C., 33° C., and 37.8° C. is determined by PMR after equilibrating for 30 minutes at each temperature.

E. Measurement of Penetration

Penetration is a measure of the firmness or consistency of a shortening. Penetration is measured by measuring the distance a given weight (47 grams) of defined shape will penetrate the shortening after falling from a height of 2 centimeters above the surface of the shortening. The firmness of the shortening is related to its composition and character, and to the temperature of the sample at the time of measurement. A standard method for measuring penetration is described in A.O.C.S. Official Method Cd. 16-60 (incorporated by reference herein). However, the method for measuring penetration values of the present invention is modified in several respects, for example, a modified Precision Universal Penetrometer (manufactured by Precision Scientific Co., Chicago, Ill.) is used to measure the penetration. The penetrating device comprising the shaft and needle (or "cone") is also modified.

Apparatus

Constant temperature boxes or room, automatically controlled to maintain the temperature at 29.5° C.±0.5° C. and 21.1° C.±0.5° C.

A specially designed needle, shaft and collar weighing 47 grams total, and described below in detail.

A titer thermometer with a temperature range of 20° to 40° C. or 15o to 35° C., reading to 0.1° C.

A sample container, either a 1 pound or 3 pound can.

A Precision Universal Penetrometer, modified as described below. The penetrometer is a mechanical device which provides in one unit a support or housing to grip and release the penetrating device (shaft and needle), a platform to support the sample, spirit level and adjustments to maintain the penetrometer in a level position and a depth gauge graduated to allow reading the depth of penetration in 0.1 millimeter units.

Specially Designed Shaft and Needle

The penetrating device comprising a shaft 1 and needle 2 (or "cone") is illustrated in FIG. 1. A 9" long hollow steel rod having a 3/16" outer diameter is used for the shaft. At the end of the shaft is a 2" long hollow stainless steel needle or cone. The point end of the needle has a 1/32" diameter, and the enlarged end has a 19/32" diameter. The needle can be unscrewed from the shaft to insert weights into the hollow needle. A magnesium collar 3 with a set screw 4 is positioned around the shaft, about 4¼" from the end opposite the needle. The collar is 7/16" in diameter and ⅛" thick. The penetrating device as a whole, including the collar, must weigh 47 grams.

Precision Universal Penetrometer Modification

In placing the shaft and needle in the housing of the instrument, the contact finger on the depth gauge is positioned below the collar. The collar is adjusted on the shaft so as to allow the depth gauge its full travel of 520 units. This is accomplished by moving the shaft upward until the needle is about two centimeters below the bottom of the housing and then sliding the collar up against the top of the housing and tightening the set screw. Next, the shaft is lowered exactly two centimeters. Using the gauge block, the depth gauge contact finger is adjusted all the way up against the collar using the adjuster screw. Remove the shaft and needle, pin the collar to the shaft and adjust the weight to 47 grams.

Conditioning of Sample

The shortening sample is tempered at 29.5°±0.5° C. for 24 hours and then stored at 21.1° C.±0.5° C. for 24 hours.

Checking the Penetrometer

Check the needle rise against the 2 centimeters gauge-block as follows: With the indicator and depth gauge in the zero position lower the penetrometer head by means of the coarse adjusting screw until the point of the needle just touches the pad block (large diameter block) then lock the screw in this position. Squeeze the clutch trigger and raise the needle to the extreme top position (collar touching the top of the housing). Check the distance between the needle point and pad by placing the 2 centimeter gauge block on the pad and carefully passing it under the needle point; the needle point should just clear the 2 centimeter gauge block. If the distance so determined is not exactly 2 centimeters, adjust the depth gauge adjusting screw until the rise and fall of the needle is exactly 2 centimeters. Set the depth gauge indicator needle to read zero by removing the face plate cover and loosening the knurled nut holding the needle in place. This check should be made once before each series of measurements.

If possible make all penetrations in a room controlled at 21.1°±0.5° C. If this is impossible, conduct the actual penetration operation immediately after the sample is removed from the 21.1° C. box. Smooth the surface of the sample by scraping, but do not disturb the contents of the can below about 0.25" of the original surface of the shortening. Immediately place the sample container on the shelf of the penetrometer, which has been leveled previously by means of the leveling screws in the base. Penetrate each sample at three or more points at least one inch apart and at least one inch from the side of the container, being certain to clean the needle by wiping with a tissue between each penetration. Under no circumstances should the needle be removed from the shaft for cleaning purposes. Insert the thermometer in the center of the sample up to its immersion mark and record temperature to 0.1° C. The temperature at which the penetration test is made should be 21.1°±0.5° C. The average of the penetrations is recorded as the uncorrected penetration. This value is corrected for penetration temperature deviation as follows: a correction of 0.5 points for every 0.1° C. above or below 21° C. should be made. If below 21.1° C. (70° F.), add the correction; if above, subtract.

Bring the indicator to zero by pulling up on the depth gauge until it stops, then squeeze the clutch trigger and again pull up on the depth gauge until it reaches zero. Release the clutch trigger. If the indicator does not read zero, adjust with the zero setting screw. By means of the coarse adjusting screw, bring the needle down until its point just touches the surface of the sample. Grasp the top of the needle, squeeze the clutch trigger and pull the needle up as far as it will go. This will raise the needle two centimeters above the sample. Release the clutch trigger. Push the depth gauge down as far as it will go.

Release the needle by squeezing the clutch trigger. In operating the clutch trigger, grasp the finger grip firmly with the forefinger, and with the thumb depress the clutch trigger quickly as far down as it will go. Pull the depth gauge up until it in tenths of a millimeter (mm/10).

F. Rheology Measurements

1. Sample Preparation

The intermediate melting sucrose fatty acid ester sample or the sucrose fatty acid ester hardstock sample is heated until it completely melts (about 91° C.) and is thoroughly mixed. Ten grams of the melted sample is weighed into a pre-heated 20 milliliter glass vial. The sample is then allowed to recrystallize at 37.8° C.±3° C. for 24 hours. After the 24 hour time period has elapsed, the sample is taken to the viscometer and the viscosity and yield stress are measured.

2. Ferranti-Shirley Viscometer Operation Procedure

A Ferranti-Shirley viscometer equipped with a 600 gram torque spring is used for the viscosity and yield stress measurements of the intermediate melting sucrose fatty acid ester sample or sucrose fatty acid ester/hardstock sample. A cone is put into place, and the viscometer temperature is adjusted to 37.8° C. The chart recorder is calibrated, and the gap between the cone and plate is set. The cone speed is checked, and the cone and plate temperatures are equilibrated to 37.8° C. The panel controls are set. Sufficient sample is placed between the plate and the cone so that the gap is completely filled. The temperature is allowed to stabilize at 37.8° C. for about 30 seconds, and then the cone rotation and recording are started. A rheogram for the sample is recorded and analyzed to determine the viscosity and yield stress. Viscosity is measured at 10 seconds$^{-1}$ after 10 minutes of steady shear. Yield stress is measured at zero time and is the stress required to achieve deformational flow.

3. Integrated Area Under Rheogram

A twenty-gram sample is melted and mixed as described above, and then about one gram of the melted sample is placed into the Ferranti-Shirley viscometer which has equilibrated at 37.8° C. The sample's shear stress is measured at 100 sec$^{-1}$ for a period of 5 minutes. Recording paper is used such that scale for chart speed is 25 millimeters per minute and the scale for shear stress is 145 dynes/cm$^2$ equals one millimeter. After the rheogram is generated, the area under the curve is integrated using hand calculations or any of several computer assisted programs for such. The integrated area is then reported in millimeters squared.

G. Liquid/Solid Stability Measurement

The intermediate melting sucrose fatty acid ester sample or sucrose fatty acid ester/hardstock sample is heated until it completely melts and is thoroughly mixed. The sample is then poured into Beckman #344062 4.4 milliliter centrifuge tubes. The tubes are immediately transferred to a 37.8° C.±0.3° C. constant temperature room and allowed to recrystallize undisturbed for 24 hours. The samples are then centrifuged at 60,000 rpm for one hour at 37.8° C. (the centrifuge and centrifuge head is previously equilibrated at 37.8° C. The force on the samples is 486,000 G's. The liquid/solid stability is then calculated as follows:

Liquid/Solid Stability =

$$\frac{100 \times (\text{total volume of sample} - \text{volume of liquid})}{\text{total volume of sample}}$$

What is claimed is:

1. A beta-prime stable tailored triglyceride hardstock comprising:
   (a) from about 45% to about 98% 2-Stearoyldipalmitin (PSP) triglycerides;

(b) from about 2% to about 55% 1-Palmitoyldistearin (PSS) triglycerides;
(c) less than about 7% tripalmitin (PPP) triglycerides;
(d) less than about 7% tristearin (SSS) triglycerides;
(e) less than about 3% diglycerides;
(f) less than about 10% total PPP and SSS triglycerides; and
(g) less than about 10% of the fatty acids of the total triglycerides and diglycerides being unsaturated;
wherein P=palmitic acid and S=stearic acid.

2. A hardstock according to claim 1 which comprises from about 60% to about 92% PSP triglycerides and from about 8% to about 40% PSS triglycerides.

3. A hardstock according to claim 2 which comprises from about 60% to about 85% PSP triglycerides and from about 15% to about 40% PSS triglycerides.

4. A hardstock according to claims 1, 2, or 3 which comprises less than about 4% PPP triglycerides; less than about 4% SSS triglycerides; less than about 3% diglycerides; and less than about 6% total PPP and SSS triglycerides.

5. A hardstock according to claim 4 which comprises less than about 1% diglycerides.

6. A hardstock according to claim 5 which comprises less than about 0.5% diglycerides.

7. A hardstock according to claim 4 wherein less than about 2% of the fatty acids of the glycerides are unsaturated.

8. A food product which contains a lipid material and which comprises from about 0.1% to about 20% of a beta-prime stable tailored triglyceride hardstock comprising:
(a) from about 45% to about 98% 2-Stearoyldipalmitin (PSP) triglycerides;
(b) from about 2% to about 55% 1-Palmitoyldistearin (PSS) triglycerides;
(c) less than about 7% tripalmitin (PPP) triglycerides;
(d) less than about 7% tristearin (SSS) triglycerides;
(e) less than about 3% diglycerides;
(f) less than about 10% total PPP and SSS triglycerides; and
(g) less than about 10% of the fatty acids of the total triglycerides and diglycerides being unsaturated;
wherein P=palmitic acid and S=stearic acid.

9. A food product according to claim 8 wherein the hardstock comprises from about 60% to about 92% PSP triglycerides and from about 8% to about 40% PSS triglycerides.

10. A food product according to claim 9 wherein the hardstock comprises from about 60% to about 85% PSP triglycerides and from about 15% to about 40% PSS triglycerides.

11. A food product according to claims 8, 9 or 10 wherein the hardstock comprises less than about 4% PPP triglycerides; less than about 4% SSS triglycerides; less than about 3% diglycerides; and less than about 6% total PPP and SSS triglycerides.

12. A food product according to claim 11 wherein the hardstock comprises less than about 1% diglycerides.

13. A food product according to claim 12 wherein the hardstock comprises less than about 0.5% diglycerides.

14. A food product according to claim 11 wherein less than about 2% of the fatty acids of the glycerides of the hardstock are unsaturated.

15. An all shortening according to claim 8 which comprises from about 3% to about 12% of the beta-prime stable tailored triglyceride hard stock.

16. A shortening according to claim 15 which comprises from about 4% to about 9% of the beta-prime stable tailored triglyceride hardstock.

17. A peanut butter according to claim 8 which comprises from about 0.3% to about 2% of the beta-prime stable tailored triglyceride hardstock.

18. A peanut butter according to claim 17 which comprises from about 0.5% to about 1.4% of the beat-prime stable tailored triglyceride hardstock.

19. A food product according to claim 8 which comprises the hardstock and a highly hydrogenated high erucic acid rapeseed oil in a ratio of from about 20:1 to about 1:1.

20. A food product according to claim 8 which comprises the hardstock and a non- or partially-digestible fatty material in a ratio of from about 1:2.9 to about 1:40.

21. A food product according to claim 20 which comprises the hardstock and a non- or partially-digestible fatty material in a ratio of from about 1:3.9 to about 1:8.8.

22. A food product according to claim 21 wherein the non- or partially-digestible fatty material is a sugar or sugar alcohol fatty acid polyester and the fatty acids have carbon chain lengths of from about 2 to about 24 carbon atoms.

23. A food product according to claim 22 wherein the fatty acids of the sugar or sugar alcohol fatty acid polyester have carbon chain lengths of about 14 to about 18 carbon atoms.

24. A food product according to claim 22 wherein the sugar of the sugar fatty acid polyester is sucrose.

25. A food product according to claim 24 wherein the sucrose fatty acid polyester has, at 37.8° C.:
(a) a viscosity of at least 0.5 poise after 10 minutes of steady shear at 10 sec.$^{-1}$; and
(b) a liquid/solid stability of at least about 30%.

26. A food product according to claim 25 wherein the sucrose fatty acid polyester has, at 37.8° C.:
(a) a viscosity of at least 5 poise after 10 minutes of steady shear at 10 sec.$^{-1}$; and
(b) a liquid/solid stability of at least 50%.

27. A food product according to claim 26 wherein the sucrose fatty acid polyester has, at 37.8° C.:
(a) a viscosity of at least about 10 poise; and
(b) a liquid/solid stability of at least 70%.

28. A food product according to claim 27 wherein the sucrose fatty acid polyester has, at 37.8° C.:
(a) a viscosity of at least about 15 poise; and
(b) a liquid/solid stability of at least about 90%.

29. A reduced calorie shortening according to claim 24 which comprises the hardstock and a sucrose fatty acid polyester in a ratio of from about 1:2.9 to about 1:40.

* * * * *

UNITED STATES PATENT AND TRADEMARK OFFICE
CERTIFICATE OF CORRECTION

PATENT NO. : 4,996,074

DATED : February 26, 1991

INVENTOR(S) : Paul Seiden; Robert L. White

It is certified that error appears in the above-identified patent and that said Letters Patent are hereby corrected as shown below:

Column 3, line 39, "ciglycerides" should read --diglycerides--.
Column 5, line 18, after "is a", insert --solvent fractionation method described in--.
Column 8, line 7, after "Fehl in" insert --"Polymorphism of 1-Behenoyldistearin and --.
Column 12, line 15, after "heated to", delete "4", insert --49° F.---.
Column 13, line 68, insert --** GCFAC (Gas Chromatography Fatty Acid Composition) is used to define the fatty acid composition of the tailored triglyceride hardstock created by the hydrogenation of the fractionated palm oil above. The method used is explained in part B. of the Analytical Method section following the examples.

*** I.V.(Iodine Value) of a fat or oil indicates the number of grams of Iodine equivalent to halogen absorbed by a 100 gram sample. Because the halogen absorbance is due to the double bonds present in the fatty acid residues attached to the glycerides, the I.V. of a fat or oil can give a general indication of solids content at a given temperature. As the fatty acid residues become more saturated, the fat or oil increases in solids content. In general, the lower the I.V. of a given fat or oil, the greater will be the solids content at a given temperature. The I.V. of a fat or oil can be determined by the AOCS Official Method Cd. 1-25, also known as the Wijs method.

****Argentation values represent the triglyceride composition in terms of positional isomers as determined by Argentation thin layer chromatography (hereinafter Argentation). Argentation uses silver nitrate as a complexing reagent in a chromatographic separation. The triglycerides separate according to the degree of unsaturation and the position of the fatty acid on the triglyceride molecule. However, chain length of the saturated fatty acids cannot be determined by this method. The specific Argentation method used to determine the triglyceride composition of the structural fat of

UNITED STATES PATENT AND TRADEMARK OFFICE
CERTIFICATE OF CORRECTION

PATENT NO. : 4,996,074          Page 2 of 2

DATED : February 26, 1991

INVENTOR(S) : Paul Seiden; Robert L. White

It is certified that error appears in the above-identified patent and that said Letters Patent are hereby corrected as shown below:

the present application is described in Section C. of the Analytical Methods section following the examples.--
Column 14, line 61, begin new paragraph with the words "The mixture's were allowed to".
Column 14, line 62, after "for" and before "minutes", insert --40--.
Column 14, line 64, begin new paragraph with the words, "The material in the four dishes was".
Column 27, line 43, after "below" delete "21", insert therefor --21.1--.
Column 27, line 61, after "it" and before "in" insert --stops. Read the dial. The reading is the penetration--.
Column 30, line 6, delete "all", insert therefor --all-purpose--.

Signed and Sealed this

Sixteenth Day of March, 1993

*Attest:*

STEPHEN G. KUNIN

*Attesting Officer*      *Acting Commissioner of Patents and Trademarks*